(12) United States Patent
Saberski (10) Patent No.: US 6,725,094 B2
(45) Date of Patent: Apr. 20, 2004

(54) APPARATUS AND METHODS FOR REDUCING PAIN AND/OR RETRAINING MUSCLES

(76) Inventor: Lloyd R. Saberski, 25 Fairwood Dr., Cheshire, CT (US) 06410

( * ) Notice: Subject to any disclaimer, the term of this patent is extended or adjusted under 35 U.S.C. 154(b) by 61 days.

(21) Appl. No.: 09/953,818

(22) Filed: Sep. 17, 2001

(65) Prior Publication Data

US 2002/0068960 A1 Jun. 6, 2002

Related U.S. Application Data

(63) Continuation of application No. PCT/US00/07863, filed on Mar. 24, 2000
(60) Provisional application No. 60/125,970, filed on Mar. 24, 1999.

(51) Int. Cl.[7] .................................................. A61N 1/36
(52) U.S. Cl. ............................ 607/46; 607/48; 607/62; 600/591
(58) Field of Search ........................... 607/1, 2, 39–41, 607/46, 48, 58, 62–64, 137, 138; 600/546, 591

(56) References Cited

U.S. PATENT DOCUMENTS

| 4,499,900 A | 2/1985 | Petrofsky et al. ............ 128/423 |
| 4,556,214 A | 12/1985 | Petrofsky et al. ............ 272/117 |
| 5,224,490 A | 7/1993 | Allen et al. .................. 128/775 |
| 5,358,519 A | 10/1994 | Grandjean ........................ 623/3 |
| 5,447,526 A * | 9/1995 | Karsdon ........................ 607/39 |
| 5,540,730 A | 7/1996 | Terry, Jr. et al. ............... 607/40 |
| 5,824,021 A | 10/1998 | Rise .............................. 607/46 |
| 5,861,017 A | 1/1999 | Smith et al. ................... 607/59 |

FOREIGN PATENT DOCUMENTS

| WO | WO 93/08874 | 5/1993 | .......... A61N/1/365 |

OTHER PUBLICATIONS

*International Search Report* corresponding to International Patent Application Ser. No. PCT/US00/07863, dated Jul. 21, 2000, 6 pages.

* cited by examiner

Primary Examiner—George R. Evanisko
(74) Attorney, Agent, or Firm—Marshall, Gerstein & Borun LLP (57) ABSTRACT

Apparatus and methods for reducing pain associated with contractions such as uterine or other muscle contractions and/or for retraining muscles are disclosed. The apparatus include a sensor for developing a signal indicative of a contraction experienced by a muscle. They also include a stimulator for applying stimulation to the patient. The apparatus also include a control unit for automatically adjusting the stimulation provided by the stimulator at least partially in response to the signal developed by the sensor.

2 Claims, 10 Drawing Sheets

APPARATUS AND METHODS FOR REDUCING PAIN AND/OR RETRAINING MUSCLES

RELATED APPLICATION

This patent is a continuation under 35 U.S.C. §120 from International Patent Application Serial No. PCT/US00/07863 which was filed on Mar. 24, 2000 which claims benefit of No. 60/125,970 filed Mar. 24, 1999.

FIELD OF THE INVENTION

The invention relates generally to pain control and muscle stimulation, and, more particularly, to apparatus and methods for reducing pain and/or retraining muscles.

BACKGROUND OF THE INVENTION

Pain management is a complex challenge for physicians, other healthcare providers and patients. Many are reluctant to use drugs for pain control, especially with pregnant women because of possible side effects for both the mother and baby.

Labor pain can last for up to 36 hours. Conventional pain medications such as epidural drug injections are usually withheld until the cervix is dilated over 4 cm. Currently, as the cervix dilates from 0–4 cm, women receive either no medication or intravenous medication such as Nisental or Demerol. Even when such medication is used, the patient can still experience significant pain. Moreover, these drugs sedate the patient at a time when the typical mother wants to be with her family and experience the miracle of birth. For these and other reasons, many women prefer to deliver their babies without drugs even in the final stages of labor.

Many non-pharmacologic methods for managing labor pain have been tried including rapid breathing, TENS (transcutaneous electrical nerve stimulation) and others. While these methods can be somewhat helpful, labor remains a painful experience for tens of millions of women around the world.

Pain specialists recognize that it is better to initiate early pain management strategies because later intervention is often more difficult. Therefore, initiating TENS therapy before the pain of a uterine contraction is felt by the patient increases TENS efficacy.

The TENS technique has been widely used for labor analgesia for over twenty years. It has also been successfully and safely used for over twenty years to treat constant, chronic pain of the sort caused by injury and disease. For example, it is widely used for back pain and sports injuries.

In the context of treating labor pain, the TENS technique employs a small battery-powered source of high frequency electrical energy applied to the skin of the mother in labor using disposable electrode pads attached to the abdomen. The TENS unit is powered and shut off on demand by an operator (i.e., either the mother, a labor coach such as the father, or an attending health care provider). A perceptive coach or health care provider could watch the output of a standard tocodynamometer (uterine contraction monitor) to predict and make adjustments to the TENS output in response to growing or declining uterine contractions. The mother, thus, receives the benefits of electrical stimulation which rises and falls with the contraction intensity without requiring her involvement in manipulating the TENS unit.

SUMMARY OF THE INVENTION

In accordance with an aspect of the invention, an apparatus is disclosed for use in reducing pain experienced by a patient. The apparatus includes a sensor structured to develop a signal indicative of a contraction experienced by the patient, and a stimulator structured to apply stimulation to the patient. In addition, the apparatus includes a control unit in communication with the sensor and the stimulator for automatically adjusting the stimulation applied by the stimulator at least partially in response to the signal developed by the sensor to reduce the pain associated with the contraction.

In accordance with another aspect of the invention, an apparatus is disclosed for use in retraining a muscle of a patient. The apparatus includes a stimulator structured to apply stimulation to the muscle of the patient in order to adjust a contraction condition of the muscle. It also includes a sensor structured to develop a signal indicative of the contraction condition of the muscle of the patient. Additionally, the apparatus is provided with a memory storing data representative of a predetermined contraction and relaxation activity for the muscle. Moreover, the apparatus is provided with a control unit in communication with the memory, the sensor and the stimulator for automatically adjusting the stimulation applied by the stimulator in response to the data stored in the memory and the signal developed by the sensor.

In accordance with another aspect of the invention, a method is provided for reducing labor pain experienced by a patient. The method includes the steps of positioning a sensor on the patient in a location for developing a signal indicative of a uterine contraction; and coupling a stimulator to the patient in a location to apply electrical stimulation reducing the labor pain. The method also includes the steps of employing the sensor to develop the signal indicative of the uterine contraction; and responding to the signal indicative of the uterine contraction by adjusting the electrical stimulation applied by the stimulator to reduce the labor pain.

In accordance with still another aspect of the invention, a method is disclosed for retraining a muscle of a patient. The method includes the steps of: (a) reading data representative of at least a portion of a predetermined contraction and relaxation activity for the muscle from a memory; and (b) measuring a contraction condition of the muscle of the patient. The method also includes the steps of: (c) comparing at least a portion of the data read from the memory to a signal representative of the contraction condition of the muscle of the patient; and (d) automatically adjusting a stimulation signal applied to the muscle by a stimulator based upon the comparison to adjust the contraction condition of the muscle.

Other features and advantages are inherent in the disclosed apparatus or will become apparent to those skilled in the art from the following detailed description and its accompanying drawings.

DESCRIPTION OF THE PREFERRED EMBODIMENTS

Figure 1:
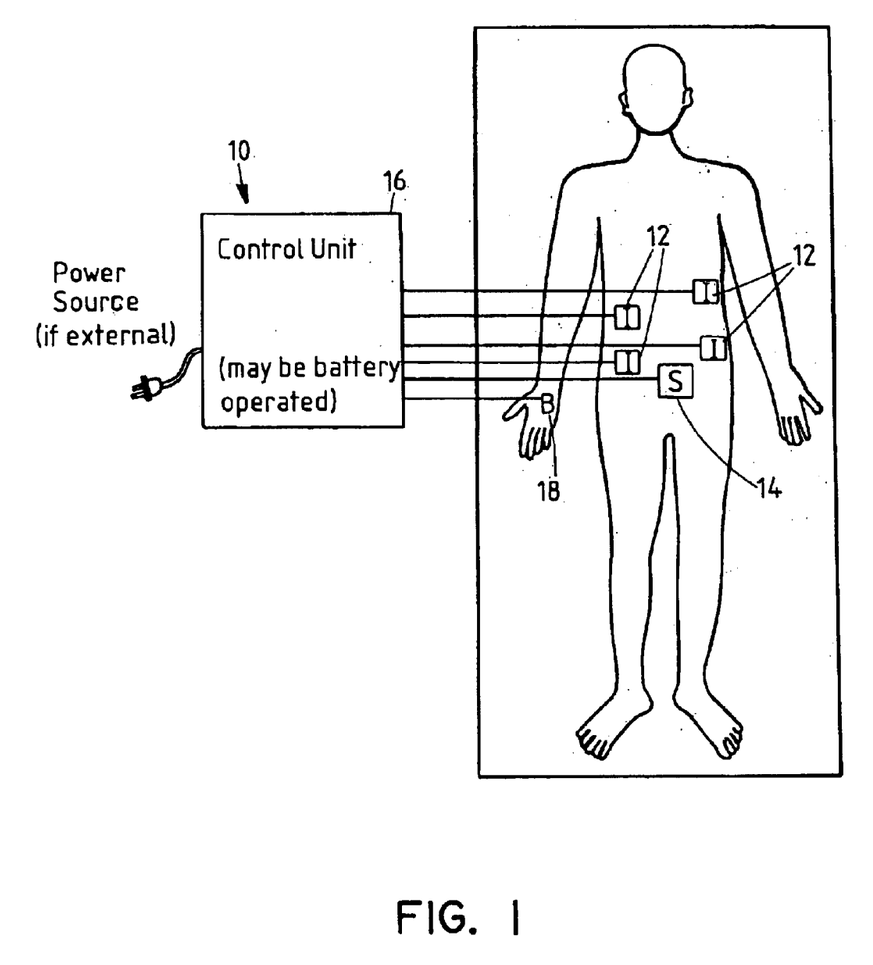
FIG. 1 is a schematic illustration of an apparatus constructed in accordance with the teachings of the instant invention and being used with a patient.

An apparatus 10 constructed in accordance with the teachings of the invention for reducing pain caused by, for example, uterine contractions during childbirth, muscle spasms such as back spasms, and/or menstrual cramps is shown in FIG. 1. Although the apparatus 10 will be described primarily in the context of controlling labor pain and retraining muscles in paralytics, persons of ordinary skill in the art will readily appreciate that the teachings of the invention are not limited to any particular environment of use. On the contrary, the teachings of the invention may be employed in any application where the pain control and/or muscle retraining capabilities it provides would be useful without departing from the scope or spirit of the invention.

By way of an overview, the disclosed apparatus 10 delivers pain controlling electrical stimulation through skin electrodes 12 or carefully placed needles in appropriate body sites. (Persons of ordinary skill in the art will readily appreciate that optimal electrode placement is not the same for all patients. Electrode placement should be determined and/or adjusted as appropriate by an attending physician or nurse). The electrical stimulation (intensity, time, etc.) delivered by the apparatus 10 is controlled by reacting to uterine contractions typically measured during labor. The timing and type of the electrical stimulation (frequency, amplitude, wavelength, duration, etc.) is preferably linked to the uterine contractions measured by the tocodynamometer or similar devices 14. Preferably, the body's uterine contraction is picked up by the tocodynamometer or similar device 14 which sends a signal through a feedback loop to the electrical stimulation device or control unit 16 which then generates and delivers the electrical stimulation at the right time and intensity. The intensity and timing of the stimulation are controlled by a closed loop feedback loop which reacts to the ever changing uterine contractile state (i.e., more intense when there is a stronger contraction, and less intense when the contractile state is lower). Advantageously, the tocodynamometer 14 detects the contraction before it is perceived by the mother. Thus, the apparatus 10 can begin treating labor pain before it actually occurs.

To use the apparatus 10, one should first explain the system to the mother and gain her agreement to utilize this pain control method. The patient's healthcare provider should, of course, be in agreement. Once agreement is reached, the sensor(s) 14 that read the muscular contraction from the uterus or other muscles, as well as the electrodes 12 that deliver the comforting electrical stimulation should be positioned on the patient at appropriate locations. The proximal ends of the electrodes 12 and sensors 14 should then be connected to the control unit 16.

The control unit 16 is then energized. The control unit 16 automatically synchronizes release of electrical stimulation with the start of uterine contractions and automatically adjusts its output according to the measured contractile intensity thereby providing pain control without constant patient or healthcare provider intervention. Because it is easier to control pain before it begins or before it becomes significant, the therapeutic electrical stimulation is delivered at the very beginning of a uterine contraction, either before it is perceived by the patient or before it becomes significant. The therapeutic electrical stimulation delivery continues until the contraction is over. More specifically, when a woman has a contraction, the stimulator will increase its output (preferably in a step-ladder fashion) as the uterus contracts and taper down the output (again, preferably in a step-ladder fashion) as the uterus relaxes.

The patient (mother) may optionally be provided with a hand-controlled switch 18 to turn the device off, turn it down, signal for help if the system is not providing benefit, or increase the electrical stimulation, thereby providing a Patient Controlled Analgesia or "P.C.A." This can be useful because each person has a different perception of pain and a different reaction to pain treatment. Therefore, a treatment that is helpful to some people may be too much or not enough for others. By allowing the patient to control some or all of the variables of intensity, frequency, duration, amplitude, etc., maximum, individualized efficacy can be achieved. In addition, providing the mother with input to the pain control apparatus may psychologically empower the patient. This sense of control may allay anxiety and fear which are large contributors to pain during labor.

Optionally, the device 10 can be structured or programmed to "learn" the patient level preferences and adjust automatically for the next cycle. Further, because labor contractions are generally rhythmic and, therefore, somewhat predictable, it is also possible to structure or program the device to "learn" the patient's individual pattern and predict a contraction before it occurs. The ability to anticipate a contraction is another way to "preemptively" deliver treatment.

The above steps may be performed in a hospital, at home, or even in a remote area, as long as electrical energy of any type is available (AC or DC current, commercial or battery power). Furthermore, the system 10 may be utilized by any care giver trained in its proper use; even people without specific medical training, provided local laws and customs allow it.

The control unit 16 should be as small as possible with as few controls as possible. It is preferably battery operated but could also operate on readily available AC current (transformed to DC) without departing from the scope or spirit of the invention. Further, a wireless system which uses available wireless technologies could be used to allow the patient maximum mobility. The freedom to move, shower, bathe, etc. can also reduce pain and allow the patient to be more comfortable.

Preferably, the control unit 16 graphically displays both the level of contraction strength and the level of therapeutic electrical impulse strength.

The impulse 12 and sensor 14 leads are preferably disposable and as few in number as possible to provide optimal benefit. Further, the impulse 12 and sensor 14 leads preferably interface with only the correct connection points on the control unit 16 to avoid any possible misuse. Both shape and color coding may be used to accomplish this end. The impulse 12 and sensor 14 leads may alternatively be reusable.

To make the product easier to use and to minimize lead tangling, the electrodes 12, 14 may be wireless.

Furthermore, wireless electrodes allow the patient to be mobile and allow women to stand and ambulate, thereby benefitting from the therapeutic effect of gravity, facilitating the movement of the fetus.

The electrodes 12 and sensors 14 are preferably placed and designed to minimize or eliminate feedback or interference between "I" (impulse) and "S" (sensor) leads.

The control unit 16 may optionally offer the operator significant manual control over the duration, intensity, frequency and amplitude of the impulse. Further, it may provide the operator with the large amounts of patient (mother and baby) monitoring information typical of a conventional fetal monitor and/or tocodynamometer. This may help the operator to customize the unit's performance for the needs of individual patients (mothers). Additionally, a more sophisticated device 16 may be useful in researching the optimal standard settings to be built into a simpler unit 16. Because each patient has a different perception of pain and a different response to treatment, customized treatment is preferred. This is true in drug therapy, where one patient may receive a different drug dosage level than another patient. This is also true with electrical stimulation. However, the ability to precisely control the electrical energy is almost infinite. A sophisticated research device 16 would facilitate general research as well as determining initial settings for a simpler unit.

The control unit 16 may be designed to interface with existing fetal or labor monitoring devices such as tocodynamometers.

Additionally, although the control unit 16 shown in FIG. 1 is a large, table top unit, persons of ordinary skill in the art will appreciate that it can be miniaturized so it can be carried by a walking mother without departing from the scope or spirit of the invention. Such a miniaturized unit preferably combines a portable tocodynamometer and TENs device in a single housing. Transmitters and receivers may optionally be used to wirelessly transfer data from the portable control unit to a display device for recording and displaying data. The miniaturized unit 16 may be provided with a port which allows the unit 16 to be physically connected to the display device when ambulation is no longer possible or desired.

Figure 2:
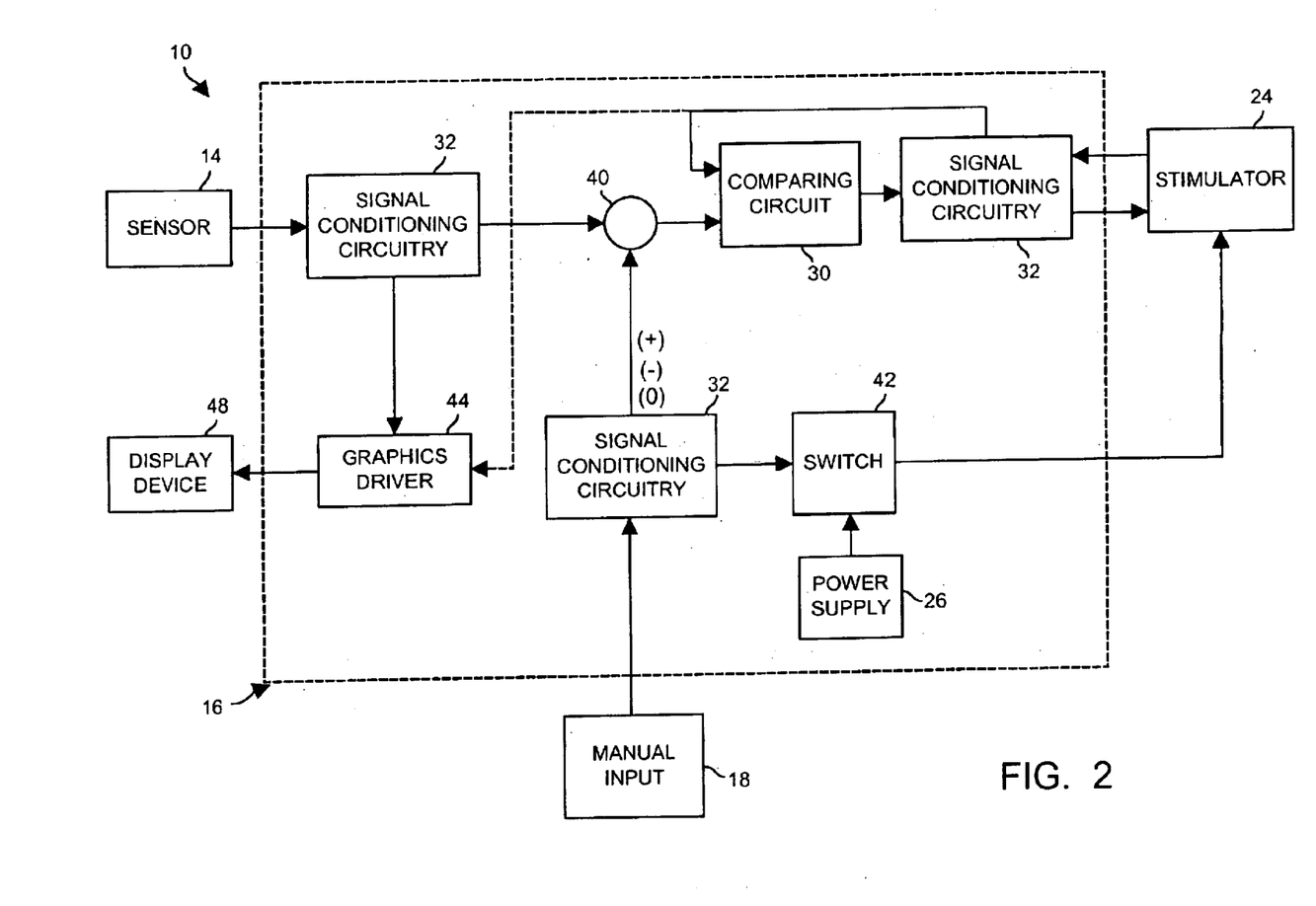
FIG. 2 is a block diagram illustrating one possible implementation of the apparatus of FIG. 1.

A more detailed illustration of an apparatus 10 constructed in accordance with the teachings of the invention is shown in FIG. 2. As shown in that figure, the apparatus 10 includes one or more sensors 14 for developing signal(s) representative of a contraction experienced by a patient. As mentioned above, although persons of ordinary skill in the art will readily appreciate that many different types of devices may be utilized to implement the sensor(s) 14, in the preferred embodiment, the sensor 14 is implemented by a conventional tocodynamometer.

For the purpose of applying stimulation to the patient, the apparatus 10 is further provided with a stimulator 24. Although persons of ordinary skill in the art will readily appreciate that many different devices (e.g., magnetic devices) may be utilized to implement the stimulator 24, in the preferred embodiment, the stimulator 24 is implemented by a conventional transcutaneous electrical nerve stimulator (TENS). Alternatively, the stimulator 24 can be implemented by an electrical contact adapted to deliver direct electrical stimulation to the spinal cord prior to, or concurrent with, drug therapy. Spinal nerve stimulation is a common pain management method, but it is not commonly used in labor. By placing the epidural catheter, the patient is prepared for delivery of drugs. However, prior to the delivery of drugs, the electrical contact 24 could be placed in the epidural space (with or without an electrolyte solution to enhance conductivity) to deliver therapeutic electrical stimulation. If effective, the electrical stimulator would reduce or eliminate the need for drugs. This direct spinal cord stimulation would most likely be used during the 4–10 cm phase of labor.

Returning to FIG. 2, for the purpose of automatically adjusting the stimulation applied by the stimulator 24 at least partially in response to the signal developed by the sensor 14 to reduce pain associated with the sensed contraction, the apparatus 10 is further provided with the control unit 16. The control unit 16 is in communication with the sensor 14 and the stimulator 16 to form a closed loop feedback loop through the patient. The control unit 16, the sensor 14 and the stimulator 16 may optionally be contained in one housing as shown in FIG. 1 and may optionally be powered from a single medical grade power supply 26. (For simplicity of illustration, not all of the power supply connections are shown in FIG. 2.) The power supply 26 may comprise a battery or an AC/DC transformer with appropriate conventional smoothing and surge protection circuitry coupled to an AC commercial power supply without departing from the scope or spirit of the invention.

In the apparatus shown in FIG. 2, the control unit 16 includes a comparing circuit 30 for comparing the signal(s) developed by the sensor 14 to signal(s) representative of the stimulation being applied by the stimulator 24 on a realtime or near realtime basis. In the analog circuit shown in FIG. 2, the comparing circuit 30 is implemented by a conventional comparator.

To ensure the signals delivered to the comparing circuit 30 are at appropriate voltage levels and strength, the control unit 16 is further provided with conventional signal conditioning circuitry 32. The signal conditioning circuitry 32 includes filters for noise reduction, amplifiers for strength adjusting and/or voltage level adjusters for ensuring all signals to be compared are appropriately scaled. Such signal conditioning circuitry is highly conventional and will not be further discussed herein.

In operation, the comparing circuit 30 receives and compares the filtered, amplified, and/or scaled signal representative of the measured contraction from the sensor 14 and the similarly conditioned signal representative of the output signal generated by the stimulator 24 to develop a difference signal. The difference signal is then passed to the stimulator 24 (after being level shifted, filtered, and/or amplified as appropriate by the signal conditioning circuitry 32). The stimulator 24 responds to a non-zero difference signal by increasing or decreasing the stimulation it is outputting (depending upon the sign of the difference signal). A signal representative of the new stimulation is returned to the comparing circuit 30 for comparison against the signal representative of the most current measured contraction state. In this way, the output of the stimulator 24 automatically tracks the measured intensity of the contraction to thereby reduce the pain experienced by the mother.

As mentioned above, the pain experience is highly individualized. Therefore, in order to enable a patient to manually increase or decrease the output level of the stimulator 24, the apparatus 10 is further provided with a manual input 18. By manipulating the input 18, the patient can input a positive, zero, or negative signal to the control unit 16. This input signal is passed through the signal conditioning circuitry 32 and input to a summer 40 of conventional design.

The summer 40 adds the input signal from the manual input 18 with the signal generated by the sensor 14. As mentioned above, the input signal from the manual input 18 can be positive, zero or negative. A positive input signal from the manual input 18 will increase the level of the signal from the sensor 14 to thereby develop a combined signal that appears to the comparing circuit 30 as if the sensor 14 has sensed a proportionally stronger contraction than was actually sensed. If the input signal from the manual input 18 is negative, it will decrease the level of the signal 14 from the sensor 14 to thereby develop a combined signal that appears to the comparing circuit 30 as if the sensor 14 has sensed a proportionally weaker contraction than was actually sensed. Of course, adjusting the level of the signal input to the comparing circuit 30 will directly adjust the level of the difference signal the comparing circuit develops and, thus, will directly effect the level of stimulation generated by the stimulator 24. Automatic control of the stimulation level will then continue as explained above based on the output of the stimulator 24 and the input signals received from the sensor 14 and the manual input 18.

Preferably, the manual input 18 is constructed so that the mother can increase or decrease the output of the stimulator 24 in five to ten percent increments. Preferably, the maximum output of the stimulator 24 is limited to a predetermined level.

As mentioned above, it is desirable to permit the patient to turn off the stimulator 24. To this end, the control unit 16 is provided with a switch 42 which may optionally be implemented by a MOSFET. The switch 42 has a first state wherein the switch 42 couples the stimulator 24 to the power supply 26. It also has a second state wherein the switch 42 isolates or disconnects the stimulator 24 from the power supply 26. The state of the switch 42 can be controlled by an input signal generated by the manual input 18.

As also mentioned above, it is also desirable to provide a visual indication of the contractions measured by the sensor 14. To this end, the control unit 16 is provided with a conventional graphics driver which is adapted to output a signal corresponding to the signal received from the sensor 14 for display on a display device 48. Optionally, the signal representative of the stimulator 24 output could also be delivered to the graphics driver 44 (see the dashed line in FIG. 2) for display on the display device 48.

Figure 3:
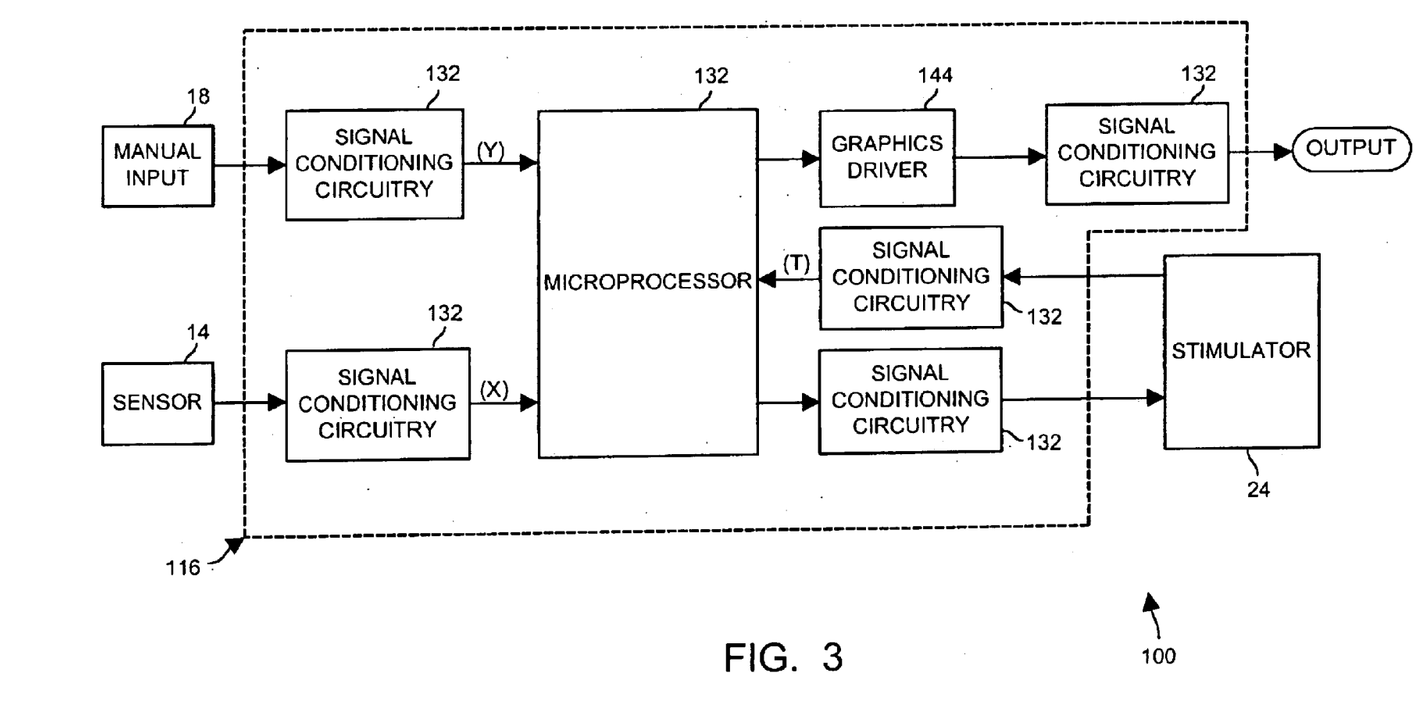
FIG. 3 is a block diagram showing another possible implementation of the apparatus of FIG. 1.

Another apparatus 100 constructed in accordance with the teachings of the invention is shown in FIG. 3. The apparatus 100 is substantially similar to the apparatus 10. However, whereas the control unit 16 of the apparatus 10 was an analog circuit, the control circuit 116 of the apparatus 100 is a microprocessor based, digital circuit. Structures bearing the same reference numbers in FIGS. 2 and 3 are identical. Similar, but not identical structures, appearing in FIGS. 2 and 3 employ reference numerals separated by one hundred (e.g., 30 in FIG. 2 is 130 in FIG. 3).

In the apparatus 100 of FIG. 3, the comparing circuit is implemented by a microprocessor 130. As a result, the signal conditioning circuitry 132 includes conventional analog to digital converters and/or digital to analog converters in addition to filtering, amplifying and/or level shifting circuitry.

Figure 4:
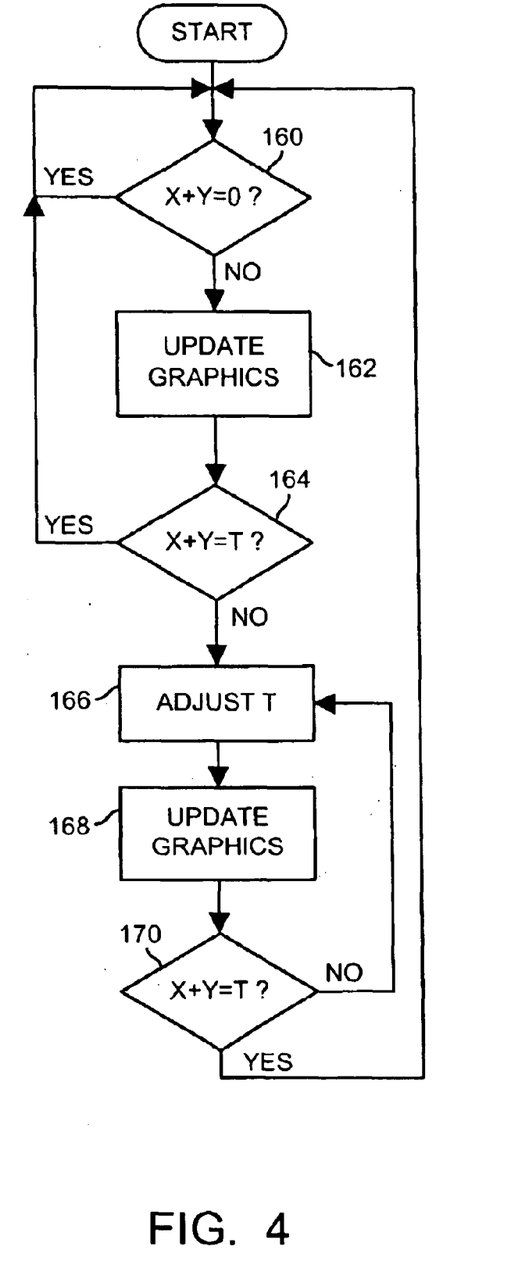
FIG. 4 is a flow chart illustrating a possible program executed by the apparatus of FIG. 3.

The microprocessor 130 is programmed to executed a program such as the exemplary program illustrated by the flowchart shown in FIG. 4. In that program, the stimulator 24 is first set to zero output and the control unit 16 determines an average baseline signal from the sensor 14 in the absence of a contraction through an initialization procedure. The microprocessor 130 then sums the input received from the manual input 18 (input "Y" in FIG. 4) with the input received from the sensor 14 (input "X" in FIG. 3) to determine if the sum of those inputs (X and Y) is non-zero (block 160). If a positive, non-zero sum is present, then the stimulator 24 must develop a non-zero output to counteract the pain associated with the sensed contraction. If a zero or negative sum is present, no output is required from the stimulator 24 because either no contraction has been sensed by the sensor 14 (i.e., X=0) and the manual input is set to zero (i.e., Y=0), or because the manual input has been manipulated to offset the signal developed by the sensor as might be the case with a patient who does not need as much pain intervention as the average patient.

Assuming that the inputs of the sensor 14 and manual input 18 create a non-zero sum, the microprocessor 130 then updates the display device with the current sensed inputs from the sensor 14 and manual input (X and Y) and the current sensed output of the stimulator 24 ("T" in FIG. 3) via the digital graphics driver 144 (block 162). The microprocessor 130 next determines whether the sensed output (T) of the stimulator 24 is equal to the sum of the inputs (X and Y) from the sensor 14 and the manual input 18 (block 164). If the output of the stimulator 24 matches the sum of the inputs (X and Y) from the sensor 14 and the manual input 18, control returns to block 160. Otherwise, control proceeds to block 166.

At block 166, the microprocessor 130 adjusts the output (T) of the stimulator 24 either up or down to equal the sum of the inputs (X and Y) from the sensor 14 and manual input 18. The microprocessor 130 then updates the display device via the graphics driver 144 (block 168) and checks the measured output (T) of the stimulator 24 to determine whether its output (T) has reached the desired level (i.e., X+Y) (block 170). The microprocessor continues to execute blocks 166–170 until the output (T) of the stimulator 24 equals the sum of the inputs (X+Y) of the sensor 14 and the manual input 18 (block 170). Control then returns to block 160.

Persons of ordinary skill in the art will appreciate that the sensed inputs (X+Y) will often change during the adjustment of the output of the stimulator 24. Therefore, control will often remain in the loop comprising blocks 166–170 for the duration of a contraction, and control will typically only return to block 160 nearer the end of a contraction when the sensed intensity is changing less rapidly.

Figure 7:
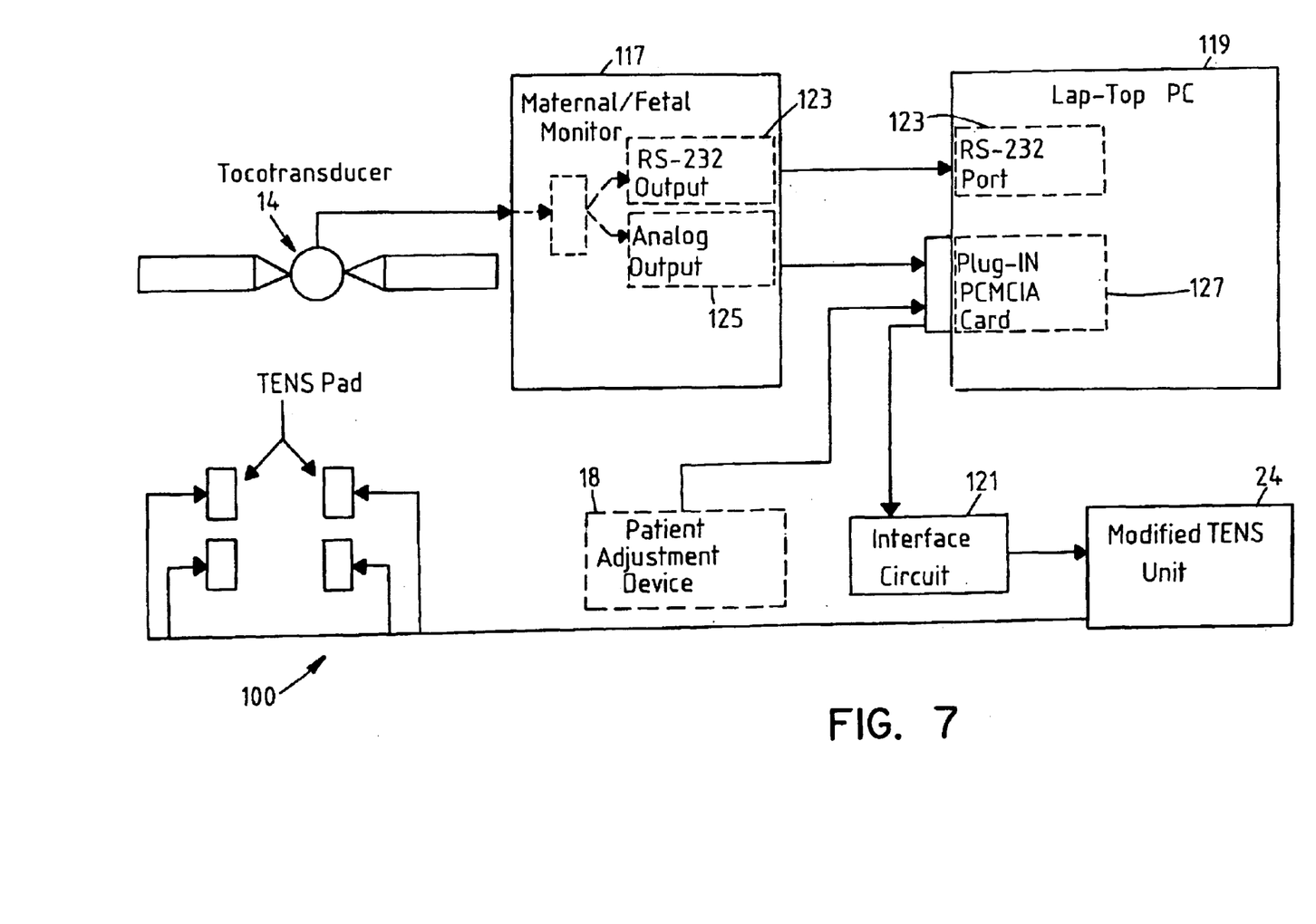
FIG. 7 is a block diagram illustrating a preferred apparatus constructed in accordance with the teachings of the invention.

A further view of the device 100 of FIG. 3 is shown in FIG. 7. As shown in FIG. 7, the control unit 116 of the apparatus 100 may be implemented by a conventional fetal monitor 117 (such as the HP/Agilent 1350A), a personal computer 119 and an interface circuit 121 for permitting the computer 119 and the TENS unit 24 to communicate. The interface circuit 121 may optionally be internal to the computer 119 or the stimulator 24. The TENS unit 24 is modified from a conventional unit to facilitate communication with, and control by, the computer 119.

As also shown in FIG. 7, the fetal monitor 117 can communicate with the personal computer 119 via RS-232 ports 123 or via an analog output 125 and a PCMCIA card 127 in a conventional fashion. Preferably, the PCMCIA card 127 is used to communicate with the interface circuit 121.

Figure 8:
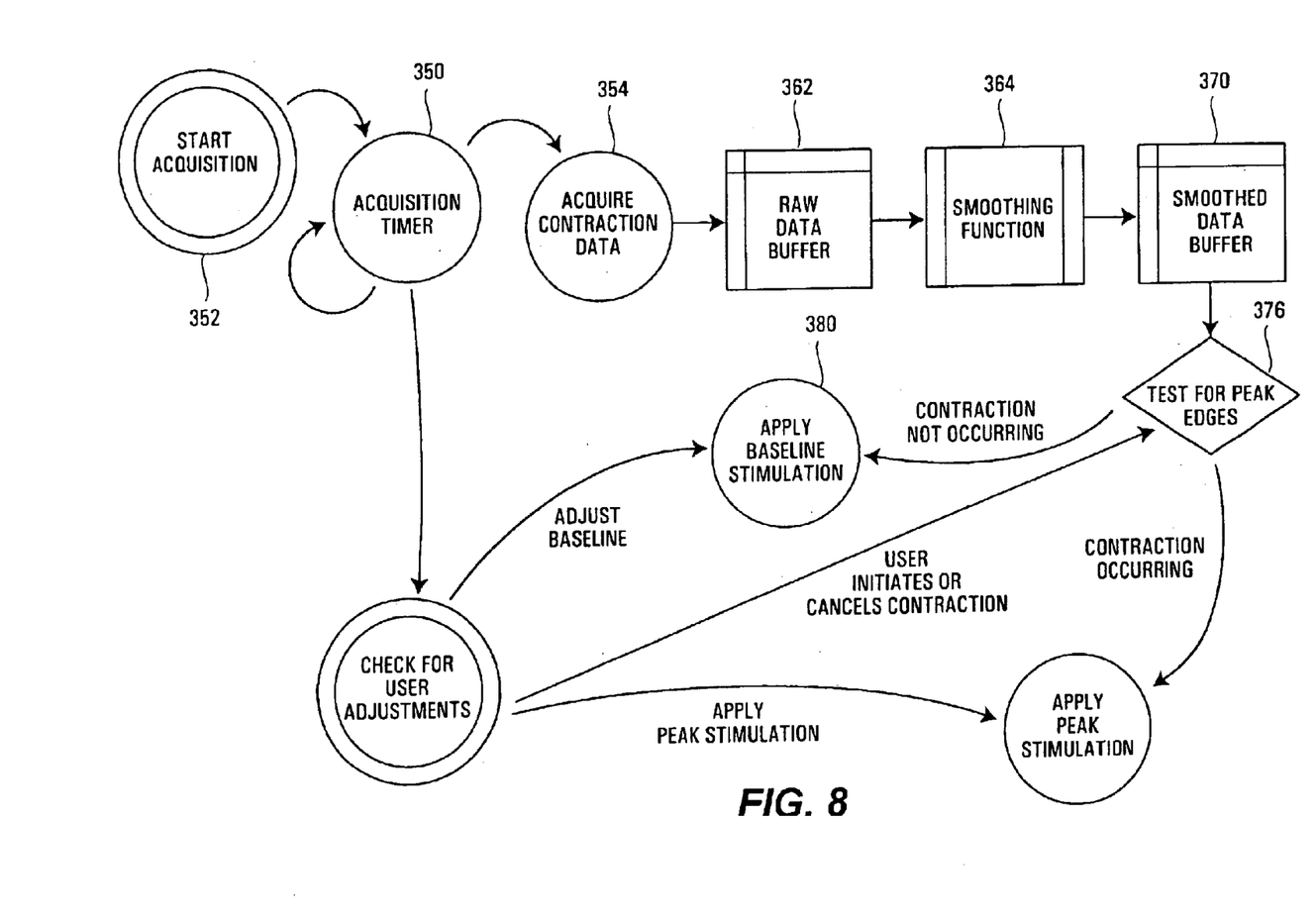
FIG. 8 is a data flow diagram illustrating the operation of the preferred software for the apparatus of FIG. 5.
Figure 9:
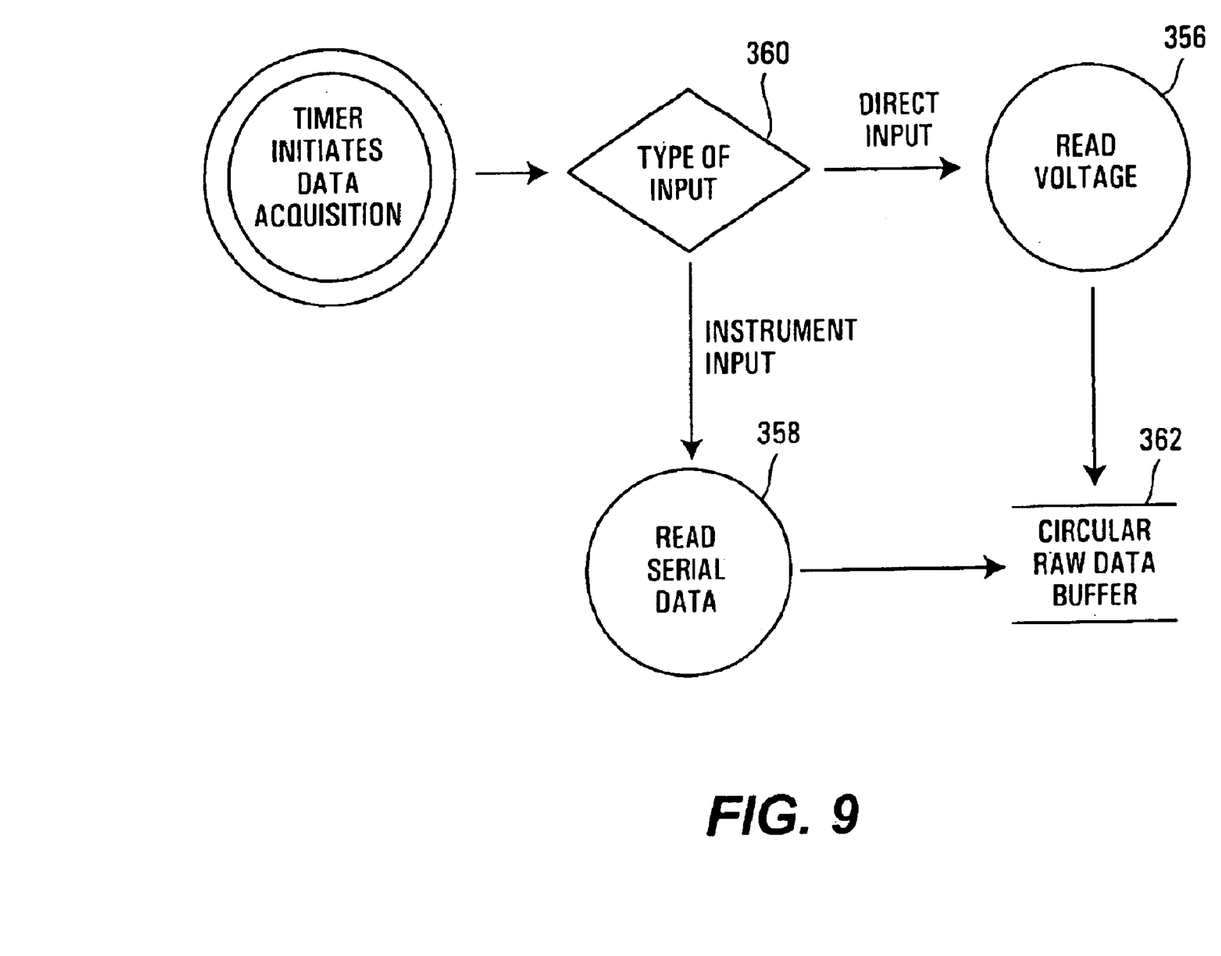
FIG. 9 is a flowchart illustrating the data acquisition process of the software of FIG. 8.
Figure 10:
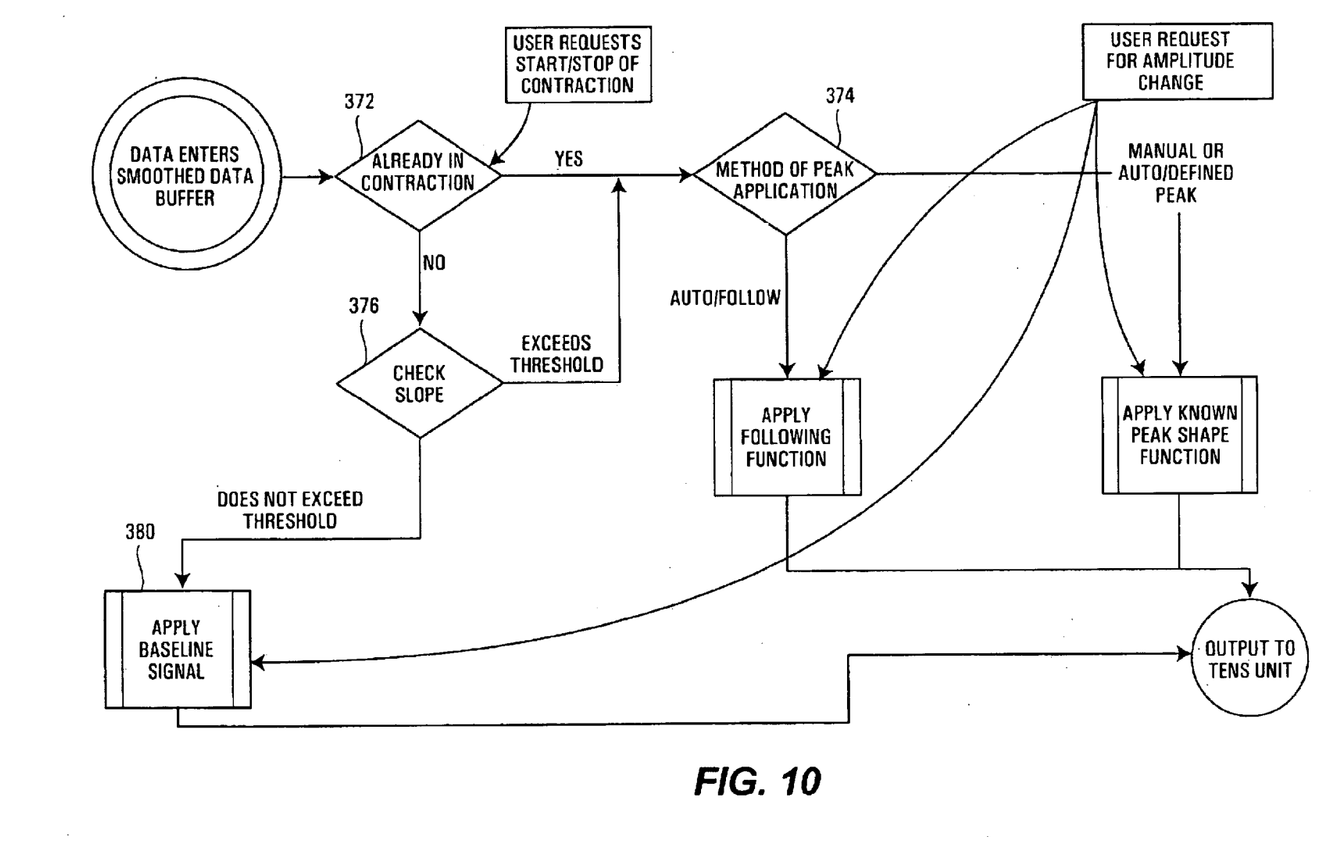
FIG. 10 is a flowchart illustrating a portion of the software of FIG. 8.

The preferred software executed by the device of FIG. 3 will now be explained in further detail in connection with FIGS. 8–10. FIG. 8 diagrammatically illustrates the overall dataflow of the software.

As shown in FIG. 8, the control unit 116 includes an acquisition timer 350. The acquisition timer 350 functions to control the frequency at which the microprocessor 130 polls its inputs for new data. The timer 250 is set to a sufficiently fine resolution to obtain enough data points to permit application of the smoothing function described below. Although persons of ordinary skill in the art will readily appreciate that other rates may be chosen, preferably the timer 250 is set to drive collection of four data points per second. This four points per second rate corresponds to the data output rate of the HP/Agilent 1350A fetal monitor, which is preferably used to implement the sensor 14.

Once the timer 350 is started (block 352), the microprocessor 130 will be driven to acquire contraction data as shown at block 354. The data for monitoring the state of the contraction may be gathered by any contraction-monitoring device which outputs a signal which is a temporal function of the progress of the contraction. For example, a tocodynamometer or an intrauterine pressure monitor (IUP) can be used in this role. As shown in FIG. 9, the device 116 can use either direct input signals from the voltage output port (which may be 0–10V) of the sensing device (block 356), or digital data which is provided by a fetal monitoring device (block 358). The digital data may be in the form of a data stream, which is transmitted by RS-232 or RS-422 protocols from the fetal monitor to the device 116. Regardless of the source of the data, once received, it is placed into a raw data buffer 362 where it can be smoothed and utilized as explained below.

The raw data buffer 362 is preferably a circular buffer whose size is selected to permit smoothing and peak detection algorithms to operate on the data. As shown in FIG. 8, a window of data from the data buffer 362 is first passed to the smoothing function 364. The smoothing function may be implemented by a Savitsky-Golay function. A Fast Fourier Transform routine may also be used to act as a low pass noise filter.

The width of the window of data which is passed to the smoothing function is limited by two criteria. First, the data window should have at least a minimum width to ensure the output functions are not delayed in time more than can be tolerated by the patient. In the currently preferred embodiment, this minimum is six seconds (e.g., twenty-four data points gathered at four points per second). Second, the window should be as wide as possible with a maximum width of one-half of the contraction peak width at half height.

As shown in FIG. 8, once the data is processed by the smoothing function 364, it is stored in a smoothed data buffer 370. As shown in FIG. 10, the software determines whether a flag has been set indicating that a contraction is in progress (block 372). If a contraction is already in progress, control proceeds to block 374. Otherwise, control proceeds to block 376.

Before proceeding further, it should be noted that the device 100 preferably has two possible modes of operation, namely, a fully automatic or follow mode, and a manual start or defined peak mode. In the fully automatic mode, the device 100 operates to form a closed feedback loop wherein the output of the stimulator 24 is automatically adjusted to track the input signals received via the sensor 14. In the manual mode, the patient (preferably) or caregiver utilizes the manual input device 18 to initiate the application of the stimulator 24, and the output of the stimulator 24 is controlled to emulate the shape of a contraction monitoring signal. In the manual mode, the input device 18 can also be used to request the end of a contraction. The duration of the stimulator output can be set by the user via device 18, or can be set based on historical data (e.g., earlier contraction(s)). More details on these modes of operation are provided below.

The input device 18 is preferably handheld. Preferably, the input device 18 allows the user to request modifications to the level of output applied by the stimulator 24 during a contraction and/or to the baseline signal generated by the stimulator 24 when a contraction is not occurring. The device 18 also preferably allows the patient to indicate the start of a contraction (which causes the device 100 to enter the contraction mode), to indicate the end of a contraction (which causes the device 100 to enter the non-contraction mode), and/or to disable all output of the stimulator 24.

Returning to FIG. 10 and assuming a contraction is not in progress (block 372), control proceeds to block 376. At block 376, the device 100 tests the slope of the data in the smoothed data buffer 270. When the slope of the data in the buffer exceeds a threshold (which is preferably adjustable), the state of the device 100 switches from the non-contraction mode to the contraction mode. In particular, if the threshold is exceeded, control proceeds to block 374 to initiate contraction level output of the stimulator 24. If the slope does not exceed the threshold, control proceeds to block 380.

At block 380 (i.e., non-contraction mode), the device 100 causes the stimulator 24 to output a low level baseline signal. This baseline signal is applied when the patient is not experiencing a contraction. The intensity of the baseline signal can preferably be set (within limits) by the patient via the input device 18. Preferably, the baseline signal is utilized in both the automatic and manual mode.

If, at block 376, the slope of the data in the smoothed data buffer 270 exceeds the threshold, or if the patient enters an input via device 18 indicating that a contraction is starting, the device 100 enters the contraction mode (block 374). When the device is in contraction mode, one of several methods may be used to determine the output characteristics of the stimulator 24. The preferred method when the device 100 is in the automatic mode is to employ an intensity following function which utilizes the input intensity of the monitored contraction as sensed by the sensor 14 as an input variable, and which generates a corresponding output signal that is sent to the stimulator 24. The preferred method when the device 100 is in the manual mode is to employ a predefined contraction peak profile generating function. This peak profile generating function is provided with a time coordinate which is referenced to the beginning of the contraction. The time coordinate is used to identify the appropriate position on the preset peak profile. An output signal representative of the intensity level of the peak profile at the identified position is then sent to the stimulator 24.

When the device 100 is in a contraction mode, the patient may request that the amplitude of the output signal of the stimulator 24 be modified to suit her comfort level via the input device 18. This request is answered by modifying the maximum amplitude of the function that generates the output signal. This modification will effect either the peak profile function (manual mode) or the intensity following function (automatic mode).

When the device 100 is in the automatic mode, the output level is determined by the intensity following function operating upon the smoothed input intensity levels in the smoothed data buffer 370. The preferred intensity following function has the following format:

$$\text{OutputLevel} = \text{BaselineAmpl} + (\text{MaxAmpl} * \text{Sensitivity} * \text{InputLevel})$$

In the above equation, the BaselineAmpl is the amplitude of the output of the stimulator 24 when there is no contraction, MaxAmpl is the maximum amplitude of the output of the stimulator 24 over the baseline amplitude, the Sensitivity variable is a user settable parameter from 0–1, and the InputLevel variable is the smoothed contraction intensity that has been normalized to a 0 to 1 scale.

In the manual mode the output of the stimulator 24 is defined by the peak profile generating function, which uses the time from the beginning of the current contraction as an input variable. This peak profile function is preferably a combination of waveforms such as Gaussian and Lorentzian waveforms. The preferred peak profile function has the following format:

OutputLevel=BaselineAmpl+MaxAmpl*

($A1$*Gaussian (time, peakwidth)+$A2$*Lorentzian (time, peakwidth))

In the above equation, BaselineAmpl and MaxAmpl are the same as defined in the preferred intensity following function equation discussed above, and A1 and A2 are scaling constants which define the combination of Gaussian and Lorentzian line shapes to emulate a contraction temporal profile. Gaussian(t, p) and Lorentzian(t, p) are conventional functions to generate a profile. In the above, A1+A2=1, the time input is time from the beginning of the peak, and the peakwidth input is the full width at half height of the contraction profile. Preferably, peak width may be adjusted by the patient.

While the peak profile function is preferably used in the manual mode, it may also be used in the automatic mode in place of the following function. If this approach is taken, the input signals for the sensor are merely employed to identify the starting and stopping times of the contractions.

From the foregoing, persons of ordinary skill in the art will readily appreciate that pain control apparatus have been disclosed for controlling pain without the use of drugs.

Specifically, the disclosed apparatus optimally deliver a well understood and commonly practiced method of pain management in a simple controlled way, which is timed to the needs of the patient with the option of being modulated by direct patient feedback. The ability to "preemptively" deliver therapy is advantageous because it is easier to control pain before it begins or before it becomes significant. This makes treatment easier and more effective. The disclosed pain control apparatus are safer than drugs.

The disclosed pain control apparatus can be used during the often long labor period prior to 4 cm of cervical dilation when drugs are not typically used, thereby providing the mother with pain relief over a longer period of time and making the entire birthing process a more pleasant experience. In other words, the disclosed pain control apparatus provide analgesia during 0–4 cm where there are few other pain relief options. Further, by minimizing drugs before, during and after delivery, there is less drug in breast milk and therefore increased safety for the baby as well as the mother.

Moreover, the disclosed pain control apparatus can also be used in conjunction with, or in place of, epidural pain control once the cervix is dilated more than 4 cm.

Use of the disclosed device is not limited to labor pain management. For example, electrical stimulation may also be in response to or coordinated with body contractions other than uterine contractions such as back and neck muscle spasms. Similarly, measurement and output response can be performed on other muscles or nerves. The device also may be of significant benefit for patients who suffer from urinary sphincter dysfunction and stress incontinence.

The disclosed pain control apparatus help women, physicians, midwives and others to make the long labor period more comfortable during the time when drugs are typically withheld. This enables the mother to be more rested and have a higher physical and mental capability to deal with the final labor period without drugs or a lower level of drugs, thereby protecting the mother and baby from drug side effects.

The disclosed pain control apparatus can eliminate the need for the traumatic, invasive epidural injection as well as the potential toxic and deleterious side effects of epidural injections. Further, the cost of epidural injection is very high.

The disclosed pain control apparatus also provide a non-drug, low cost, simple pain management system that is available for hospital and/or home delivery in both industrialized countries as well as underdeveloped countries where financial resources and the availability of highly skilled anesthesiologists are generally quite limited.

The disclosed pain control apparatus further provide "preemptive" pain relief prior to the actual onset of pain or prior to experiencing a significant level of pain. While in labor, women's uterine contractions are typically monitored with a tocodynamometer. This and other similar devices can sense the beginning of a uterine contraction before it is perceived by the patient. By linking a tocodynamometer (or similar device) with the TENS unit so that the TENS is applied or increased in a coordinated way with a uterine contraction, efficacy is enhanced. Furthermore, the patient, nurse, midwife or family member is totally or at least partially relieved from constantly operating the TENS device.

Although the apparatus 10, 100 of FIGS. 1–4 have been described for use in controlling pain associated with contractions such as uterine contractions experienced during labor and spasms (i.e., muscle spasms in the back or neck), the teachings of the present invention may also be used in muscle retraining of, for example, paraplegics, quadriplegics, stroke sufferers, or other patients (e.g., patients with paralytic intestines and dysfunctional urinary sphincters).

Figure 5:
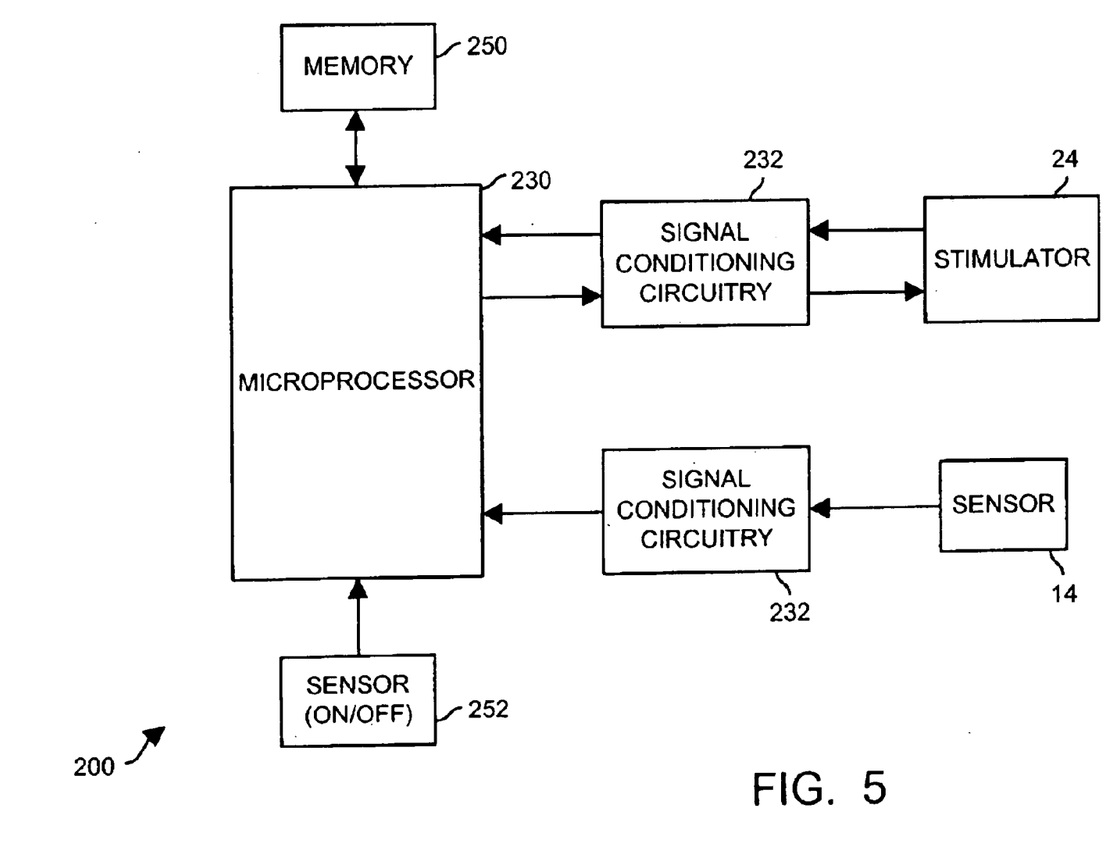
FIG. 5 is a block diagram of another apparatus constructed in accordance with the teachings of the invention.

An apparatus 200 constructed in accordance with the teachings of the invention for performing muscle retraining is shown in FIG. 5. Like the apparatus 10, 100 described above, the apparatus 200 includes a stimulator 24 which is preferably implemented by a TENS device. The stimulator 24 of the apparatus 200 is controlled to apply stimulation to the muscle to be retrained in order to adjust a contraction condition of the muscle. The contraction condition of the muscle refers to any state of contraction between totally relaxed and completely contracted, and is preferably inclusive of those two extremes.

For the purpose of developing a signal indicative of the contraction condition of the muscle to be retrained, the apparatus 200 is further provided with a sensor 14. The sensor 14 of the apparatus 200, like the sensors 14 of the apparatus 10, 100, is preferably implemented by a tocodynamometer.

For the purpose of storing data representative of a predetermined contraction and relaxation activity to be performed by the muscle to be retrained, the apparatus 200 is preferably provided with a memory 250. The memory 250 can be implemented by a conventional read only memory (e.g., EEPROM, CD ROM, etc.), but preferably is implemented by a read/write memory such as a SRAM, hard drive, or other conventional memory device. The predefined contraction and relaxation activity can be any desired activity, but typically will comprise data representative of a curve increasing the contraction state of the muscle from a relaxed condition to a fully flexed or contracted condition and then decreasing the contraction state of the muscle from the fully flexed or contracted condition to the relaxed condition. Preferably, the predetermined contraction and relaxation activity will allow for relaxation of the muscle in a gradual manner, thus, facilitating the natural activity of activating reciprocal muscle groups to obtain flexion then extension, which is typical for activity for walking.

In order to automatically adjust the stimulation applied by the stimulator 24 to the muscle being retrained in response to the data stored in the memory 250 and the output of the sensor 14, the apparatus 200 is further provided with a control unit 230. As shown in FIG. 5, the control unit 230 is in communication with the memory 250, the stimulator 24 and the sensor 14. As with the apparatus 10, 100, signal conditioning circuitry 232 is provided for filtering, level shifting, amplifying and/or converting signals passing between two or more of the control unit 230, the stimulator 24 and/or the sensor 14.

The control unit 230 includes a comparing circuit for comparing the signal developed by the sensor 14 to data from the memory 250. Persons of ordinary skill in the art will readily appreciate that the comparing circuit can be implemented in many ways without departing from the scope or spirit of the invention. For example, the comparing circuit can be implemented by a comparator such as that shown in FIG. 2. However, in the preferred embodiment shown in FIG. 5, the comparing circuit is implemented by a microprocessor 230.

In order to enable a partially paralyzed individual to initiate the retraining process after the sensor 14 and stimulator 24 are affixed to the muscle or muscle group to be stimulated, the apparatus 200 is preferably provided with a sensor 252. Persons of ordinary skill in the art will readily appreciate that the sensor 252 can be implemented in many ways without departing from the scope or spirit of the invention. For example, the sensor 252 can be implemented by a blowtube or other conventional sensor capable of sensing, for example, tongue movement, eyeball movement, or movement of another appendage.

Figure 6:
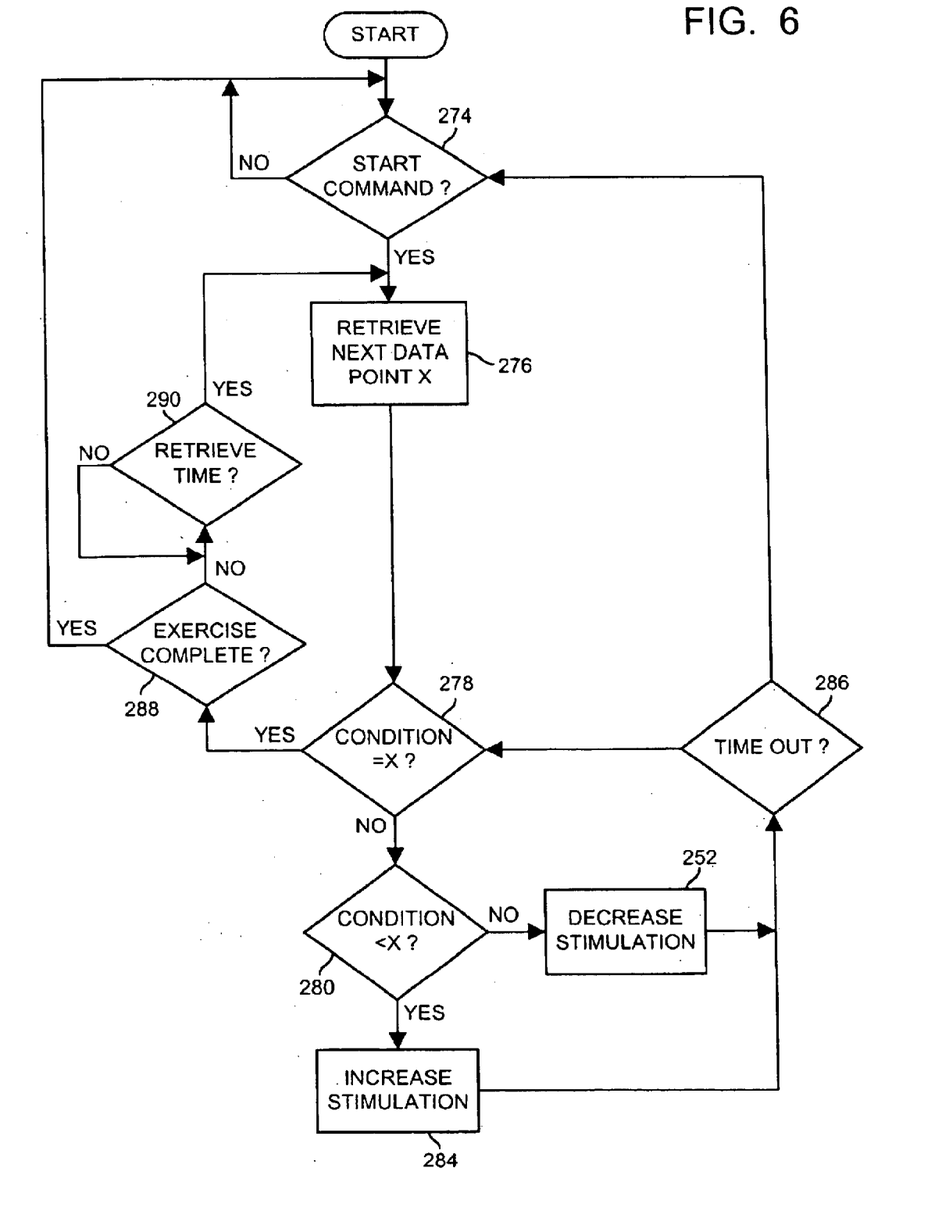
FIG. 6 is a flow-chart illustrating a possible program executed by the apparatus of FIG. 5.

An exemplary program which can be executed by the microprocessor 230 is shown in FIG. 6. After performing various conventional initialization processes such as setting the output of the stimulator 24 to zero, the microprocessor 230 enters a loop wherein it awaits a start command from the sensor 252 (block 274). Once that start command is received (block 274), the microprocessor 230 retrieves one or more data values from the memory 250 corresponding to the predetermined contraction and relaxation activity (block 276). The microprocessor 250 then compares the input received from the sensor 14 (i.e., a signal representative of a measured contraction condition of the muscle) to the first data point in the predetermined contraction and relaxation activity (block 278). If the input signal received from the sensor 14 and the first data point are substantially equal (block 278), control proceeds to block 288. Otherwise control proceeds to block 280.

At block 280, the microprocessor 230 determines if the measured contraction condition of the muscle is less than the contraction condition specified by the data point from the memory 250. If so, the microprocessor 250 increases the output of the stimulator 24 by a predetermined amount (block 284). Otherwise, the microprocessor decreases the output of the stimulator 24 by a predetermined amount (block 282). Regardless of whether the stimulator 24 has been instructed to increase or decrease its output, the microprocessor 230 determines whether a timeout condition has been reached (block 286). A timeout can occur, for example, if the desired muscle contraction state is not reached within a predetermined time (e.g., stimulator 24 is not connected properly, etc.). Control continues to loop between blocks 278–286 until the sensed contraction state substantially equals the contraction state specified by the data point from memory (block 278), or until a timeout condition (block 286) is reached. If a timeout condition occurs (block 286), the exercise terminates until a new start command is received (block 274).

If, on the other hand, the loop defined by blocks 278–286 is exited at block 278, the microprocessor 230 determines whether the exercise is complete (i.e., the muscle being retrained has entered the contraction/relaxation state specified by every data point in the predetermined contraction and relaxation activity) (block 288). If so, control returns to block 274 where the microprocessor 230 awaits a command to start another exercise. Otherwise, control proceeds to block 290.

At block 290, the microprocessor 230 determines whether it is time to advance to the next point in the contraction and relaxation activity. When the time to move to the next stage of the activity is reached (block 290), control proceeds to block 276 where the next data point in the activity is retrieved. The process then continues as explained above by comparing the measured contraction condition of the muscle to the desired contraction condition specified by the new data point (block 278) and adjusting the output of the stimulator 24, if necessary. Control continues to loop through blocks 276–290 until the exercise specified by the predetermined contraction and relaxation activity has been performed by the muscle being retrained (block 288), or until a timeout error occurs (block 286).

Although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed is:

1. A method for reducing labor pain experienced by a patient during contractions, using nerve stimulation, the method comprising the steps of:

positioning a sensor on the patient in a location for developing a signal indicative of a uterine contraction;

coupling a stimulator to the patient in a location to apply electrical nerve stimulation reducing the labor pain;

employing the sensor to develop the signal indicative of the uterine contraction;

receiving a signal representative of the electrical stimulation applied by the stimulator;

receiving a manual input signal representative of an adjustment to a level of stimulation; and adjusting the electrical nerve stimulation developed by the stimulator based upon the signal indicative of the uterine contraction, the signal representative of the electrical stimulation applied by the stimulator, and the manual input signal.

2. A method as defined in claim 1, wherein adjusting the electrical stimulation developed by the stimulator comprises:

generating a sum signal based on the signal indicative of the uterine contraction and the manual input signal;

comparing the sum signal to the signal representative of the electrical stimulation applied by the stimulator; and adjusting the electrical nerve stimulation developed by the stimulator based upon the comparison.

* * * * *